US008070764B2

United States Patent
Ross et al.

(10) Patent No.: US 8,070,764 B2
(45) Date of Patent: Dec. 6, 2011

(54) MICROKERATOME WITH A DETACHABLE HEAD

(75) Inventors: Rod Ross, Mission Viejo, CA (US);
Gregg Hughes, Mission Viejo, CA (US);
James R. Dennewill, Cerritos, CA (US)

(73) Assignee: Med-Logics, Inc., Laguna Hilla, CA (US)

( * ) Notice: Subject to any disclaimer, the term of this patent is extended or adjusted under 35 U.S.C. 154(b) by 1238 days.

(21) Appl. No.: 11/366,043

(22) Filed: Mar. 1, 2006

(65) Prior Publication Data

US 2007/0208362 A1    Sep. 6, 2007

(51) Int. Cl.
*A61F 9/00*    (2006.01)
(52) U.S. Cl. ........................................ 606/166
(58) Field of Classification Search .............. 606/166,
606/167, 172, 107, 161, 4, 5; 206/363, 349,
206/355, 249, 91, 250, 267, 438, 775, 804,
206/228, 493, 562, 566, 359, 352, 360; 30/330–339,
30/62, 63, 65, 67, 70, 71, 535, 539, 541,
30/105, 314, 379, 208, 258, 6
See application file for complete search history.

(56) References Cited

U.S. PATENT DOCUMENTS

| 4,082,386 | A | * | 4/1978 | Beasley, Jr. .................. 312/204 |
| 6,254,619 | B1 | | 7/2001 | Garabet et al. ................ 606/166 |
| 6,569,174 | B1 | | 5/2003 | O'Donnell, Jr. ............... 606/166 |
| 6,702,832 | B2 | * | 3/2004 | Ross et al. ...................... 606/166 |
| 7,056,327 | B2 | * | 6/2006 | Levesque et al. .............. 606/166 |
| 2003/0045895 | A1 | | 3/2003 | Ross et al. ...................... 606/166 |
| 2003/0139755 | A1 | | 7/2003 | Dybbs ............................ 606/166 |
| 2004/0010277 | A1 | | 1/2004 | Levesque et al. .............. 606/166 |
| 2004/0059361 | A1 | | 3/2004 | Feingold et al. ............... 606/166 |
| 2005/0055041 | A1 | | 3/2005 | Woods ........................... 606/166 |

FOREIGN PATENT DOCUMENTS

| EP | 1 126 804 B1 | 8/2001 |
| WO | WO 98/27901 | 7/1998 |
| WO | WO 02/17834 A2 | 3/2002 |

* cited by examiner

*Primary Examiner* — S. Thomas Hughes
*Assistant Examiner* — Jocelin Tanner
(74) *Attorney, Agent, or Firm* — The Eclipse Group LLP; David P. Gloekler

(57) ABSTRACT

A microkeratome that includes a latch assembly that couples a head to a hand piece. The latch assembly allows the head to be readily detached from the hand piece and sterilized. There is no need to also sterilize the hand piece. The microkeratome also has a ring assembly that is coupled to the head and the hand piece. The ring assembly may include a fastener that can be unfastened to allow the hand piece and head to be detached from the ring, even while the ring assembly is fixed to a cornea. The hand piece includes a motor that moves the blade across the ring. The microkeratome may have an aspiration connector with a collar that limits the travel of the blade the and thickness of a resulting lamella flap. The aspiration connector can be replaced with a collar of a different diameter to produce a flap with a different thickness.

7 Claims, 6 Drawing Sheets

MICROKERATOME WITH A DETACHABLE HEAD

BACKGROUND OF THE INVENTION

1. Field of the Invention

The present invention relates to a medical device that is used to cut a cornea.

2. Background Information

There have been developed a number of different surgical techniques to correct hyperopic or myopic conditions of a human eye. U.S. Pat. No. 4,840,175 issued to Peyman discloses a procedure wherein a thin layer of a cornea is cut to expose the stroma layer of the cornea. A laser beam is then directed onto the exposed corneal tissue in a predetermined pattern. The laser beam ablates corneal tissue and changes the curvature of the eye. This procedure is sometimes referred to as Laser in situ Keratomileusis (LASIK).

U.S. Pat. No. Re 35,421 issued to Ruiz et al. discloses a device for cutting a cornea in a LASIK procedure. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while the blade moves in a reciprocating transverse direction to cut the eye. The device can create a lamella flap of the cornea which is flipped back so that the stromal bed of the cornea can be ablated with a laser.

U.S. Pat. No. 6,051,009 issued to Hellenkamp et al. discloses a microkeratome that is sold under the trademark HANSATOME. The HANSATOME microkeratome moves the blade in an arcuate path about the cornea. The HANSATOME includes a disposable blade assembly that can be loaded and removed from the device. The blade assembly includes a blade holder that is attached to a cutting blade. The blade holder has a recess that receives the end of a drive shaft. Rotation of the output shaft moves the blade in an arcuate path, and moves the blade in a back and forth motion to create the lamella flap of the cornea.

Microkeratomes have three primary components, a hand piece that contains a motor, a head that holds the blade, and a ring that applies a suction to maintain the position of the microkeratome relative to the cornea. Because the microkeratome is in contact with patient tissue it must be cleaned after each procedure, typically in an autoclave. The motor and accompanying gears are typically enclosed by a housing of the hand piece. The enclosed nature of the assembly increases the difficulty of cleaning the internal components of the hand piece. Additionally, the autoclave process may degrade the hand piece motor after a number of procedures and cleaning cycles. It would be desirable to provide a microkeratome that does not require the hand piece to be sterilized after each surgical procedure.

The blades used to cut tissue are replaced after each procedure. The replacement blades are typically loaded into the head of the microkeratome with a pair of tweezers. The blade must be loaded accurately so that a drive pin of the motor assembly is inserted into a corresponding slot of a blade holder. Accurately loading the blade with tweezers can be a time consuming process. It would be desirable to provide a blade package that can be used to accurately load a blade into a microkeratome in a time efficient manner.

A complication may occur while the microkeratome is cutting the lamella flap. It may be desirable to remove the microkeratome in the middle of a cut. Removing the microkeratome requires releasing the vacuum of the suction ring. Releasing the vacuum allows the cornea to move back to its original shape. Movement of the cornea will also cause the blade to move. Movement of the blade may cause damage to the cornea. It would be desirable to provide a microkeratome that allows a surgeon to remove a blade while the suction ring is still fixed to the cornea. It would also be desirable to provide a microkeratome that allows the surgeon to vary the thickness of the lamella flap hinge.

BRIEF SUMMARY OF THE INVENTION

A microkeratome that has a head coupled to a hand piece by a latch assembly. The head holds a blade.

DETAILED DESCRIPTION

Disclosed is a microkeratome that includes a latch assembly that couples a head to a hand piece. The latch assembly allows the head to be readily detached from the hand piece and sterilized. There is no need to also sterilize the hand piece. The microkeratome also has a ring assembly that is coupled to the head and the hand piece. The ring assembly may include a fastener that can be unfastened to allow the hand piece and head to be detached from the ring, even while the ring assembly is fixed to a cornea.

The hand piece includes a motor that moves the blade across the ring. The microkeratome may have an aspiration connector with a collar that limits the travel of the blade and the thickness of a resulting lamella flap. The aspiration connector can be replaced with a collar of a different diameter to produce a flap with a different thickness. This allows a surgeon to select a flap hinge thickness.

The blade may be loaded into the microkeratome with a blade shuttle. The blade shuttle may have a plunger that pushes the blade into the microkeratome head. The movement of the plunger may be limited by a stop within the shuttle. The stop assists in accurately locating the blade within the head.

Figure 1:
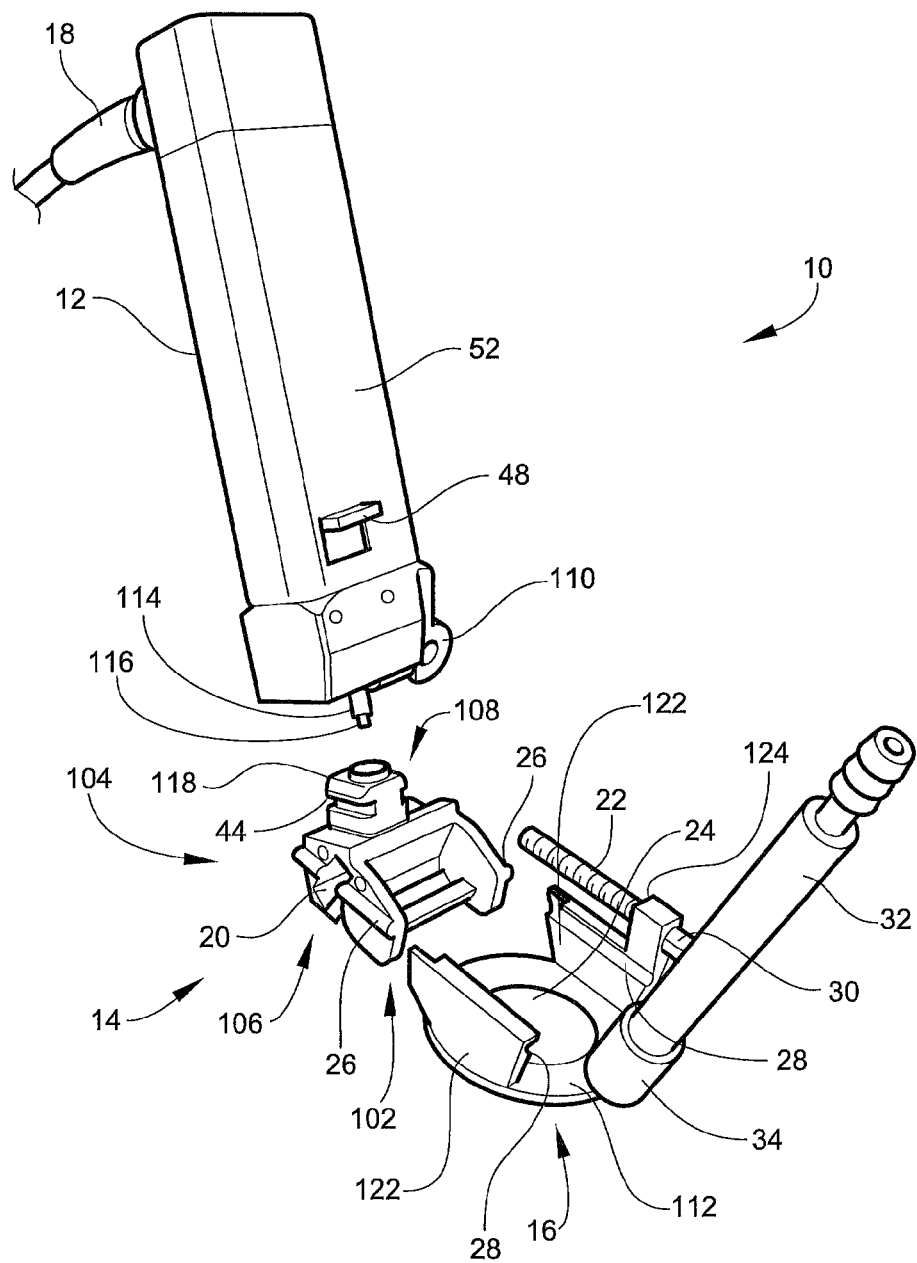
FIG. 1 is an exploded view of a microkeratome assembly of the present invention.
Figure 2:
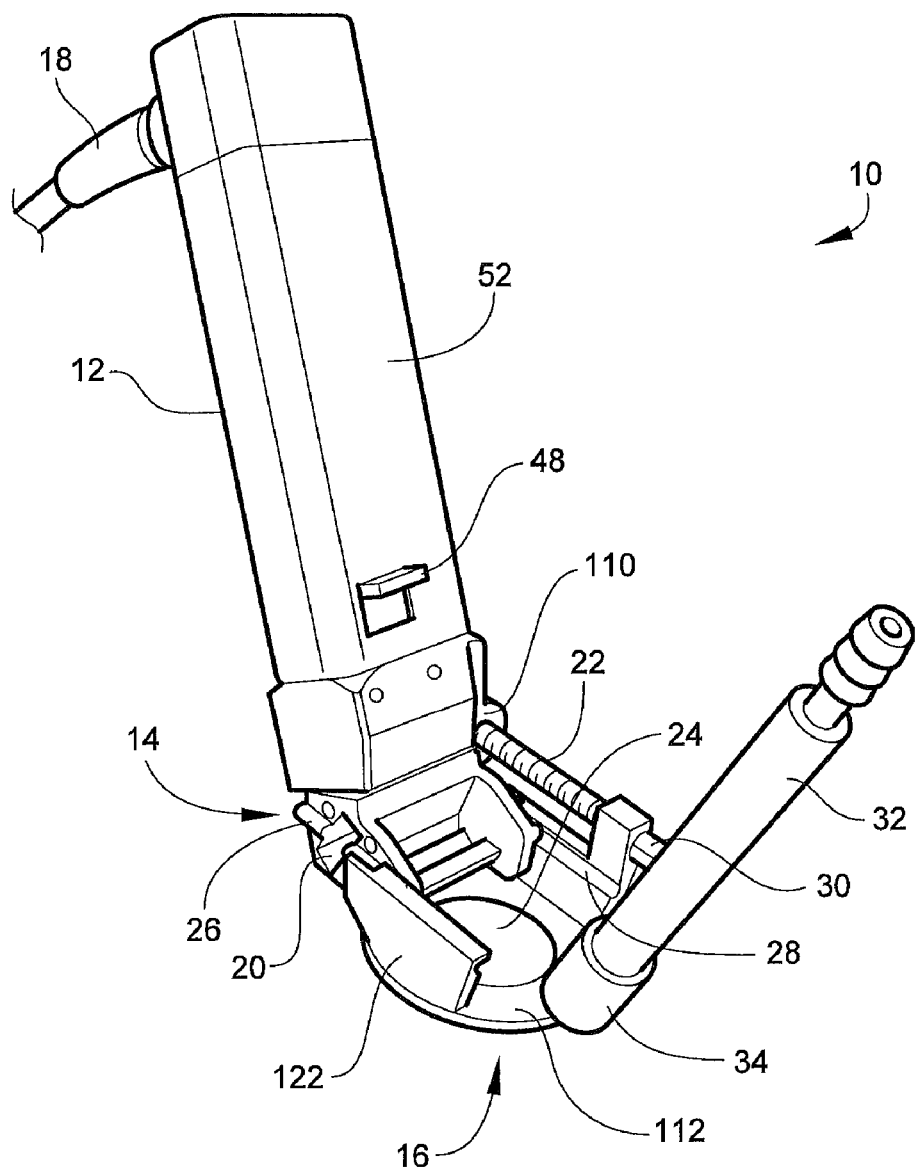
FIG. 2 is a perspective view of the microkeratome.

Referring to the drawings more particularly by reference numbers, FIGS. 1 and 2 show an embodiment of a microkeratome 10 of the present invention. The microkeratome 10 includes a hand piece 12 that is connected to a head 14 and a ring assembly 16. The microkeratome 10 is typically used to cut a lamella flap in a cornea as part of a LASIK procedure. The ring assembly 16 may be attached to a source of vacuum to create a suction pressure between the ring 16 and the cornea. The suction pressure fixes the microkeratome 10 to the cornea. The hand piece 12 has a wire assembly 18 that is connected to an electrical console (not shown). The console provides electrical power to actuate the microkeratome 10.

The head 14 generally includes a front side 102, a rear side 104, a bottom side 106, and a top side 108. The head 14 has a blade cavity 20 that can receive a blade, or a blade and a blade holder to which the blade is mounted (not shown). The ring assembly 16 may include a helical gear 22 that is coupled to the hand piece 12. For example, the helical gear 22 may be coupled to an internal gear (not shown) of the hand piece 12 at a coupling location 110. The hand piece 12 includes a motor (not shown) that cooperates with the helical gear 22 to move the head 14 and blade in a linear direction across an opening 24 of the ring assembly 16. The opening 24 is formed through a top surface 112 of the ring assembly 16 that faces the bottom side 106 of the head 14 and its blade. The cornea may protrude through this opening 24.

To accurately guide the head 14 and the blade along the linear direction, the head 14 and ring assembly 16 may have one or more corresponding linear bearing members such as, for example, one or more corresponding tongues 26 and grooves 28, respectively, that create linear bearings. In the illustrated example, the tongues 26 are formed on the head 14 and the grooves 28 are formed on the ring assembly 16. Alternatively, the tongues 26 may be formed on the head 14 and the grooves 28 may be formed on the ring assembly 16. In another alternative, the head 14 may include a tongue 26 that movably engages a corresponding groove 28 of the ring assembly 16, and the head 14 may also include a groove 28 that is engaged by a corresponding tongue 26 of the ring assembly 16.

The hand piece 12 may contain another motor (not shown) that moves the blade in a lateral reciprocating (or oscillating) manner (i.e., orthogonal or transverse to the linear direction along which the head 14 moves) so that the blade cuts corneal tissue and creates a lamella flap. For example, this other motor may drive the rotation of a shaft 114 that includes an eccentric cam or pin 116. When the head 14 is attached to the hand piece 12 in this example, the shaft 114 extends through a coupling member 118 generally disposed at or near the top side 108 of the head 14 and the eccentric pin 116 engages a slot (not shown) of the blade (or blade holder). The coupling member 118 or some other portion of the structure of the head 14 may have a groove 44 utilized to attach the head 14 to, and detach the head 14 from, the hand piece 12 in a manner described below. The coupling member 118 of the head 14 may be oriented such that the hand piece 12 is oriented at a non-zero angle relative to the top surface 112 of the ring assembly 16.

The ring assembly 16 may include one or more side walls 122 that extend upward from the top surface 112 of the ring assembly 16 on either side of the opening 24 of the ring assembly 16. The linear bearing member(s) associated with the ring assembly 16 (e.g., tongues 26 and/or grooves 28 as described above) may be formed in the side wall(s) 122 as illustrated in the example of FIGS. 1 and 2. A bore 124 may be formed in one of the sidewalls 122 to receive the helical gear 22. The ring assembly 16 may further include a nut 30 that is attached to the helical gear 22. The nut 30 can be removed to allow the hand piece 12 and head 14 to be detached from the ring assembly 16. This allows the hand piece 12, head 14 and blade to be removed even while the ring 16 is applying suction to a cornea. By way of example, the microkeratome 10 may be actuated to initiate cutting of a cornea by the blade. A complication may occur which causes the surgeon to de-actuate the microkeratome 10 and stop the cutting process. Under suction the ring 16 flattens out the cornea. If the suction is removed the cornea may move back to its natural shape. This movement may cause undesirable movement between the blade and corneal tissue. The nut 30 allows the hand piece 12, head 14 and the blade to be removed from the cornea without removing the suction of the ring 16.

The ring assembly 16 may include an aspiration connector 32. The aspiration connector 32 is connected to an aspiration tube (not shown) and is coupled to aspiration openings (not shown) in the ring. The aspiration connector 32 may have a collar 34 that limits the travel of the head 14 and the blade. The aspiration connector 32 may have a threaded shaft (not shown) that screws into a corresponding threaded opening (not shown) of the ring assembly 16.

Figure 3:
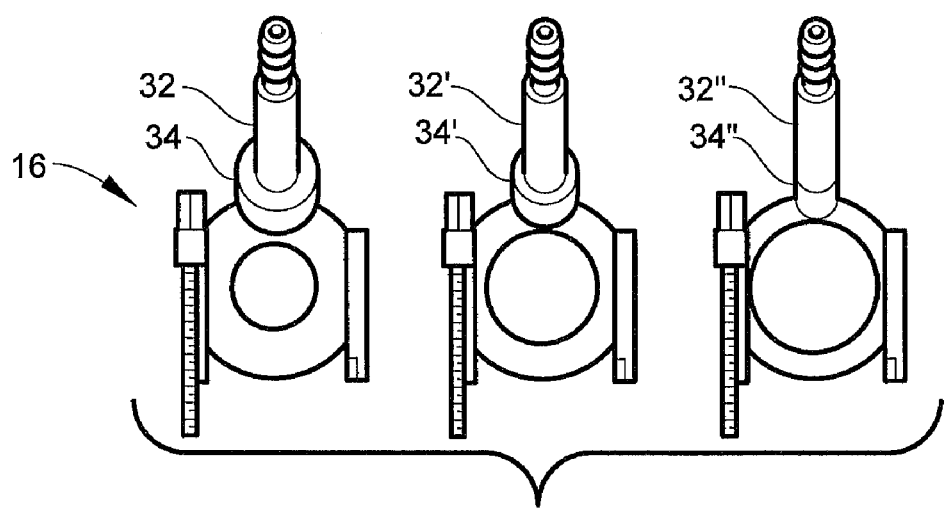
FIG. 3 is a top view showing three different aspiration connectors.

FIG. 3 shows a plurality of aspiration connectors 32, 32' and 32" that each have collars 34, 34' and 34". Each collar 34, 34' and 34" has a different diameter. The thickness of the lamella flap can be varied by attaching different connectors 32, 32' or 32" to the ring assembly 16. For example, connector 32 may create a relatively thin flap. Connector 32' may create a thicker flap and connector 32" may create an even thicker flap. The different connectors 32, 32' and 32" allow the surgeon to vary the thickness of a lamella flap.

Alternatively, the helical gear 22 can provide a stop function. The stop function may be provided by the end of the threads near the fastener 30. The stop function could also be provided by a nut attached to the threads of the gear 22. The size of the flap hinge can be varied by changing gears 22.

Figure 4:
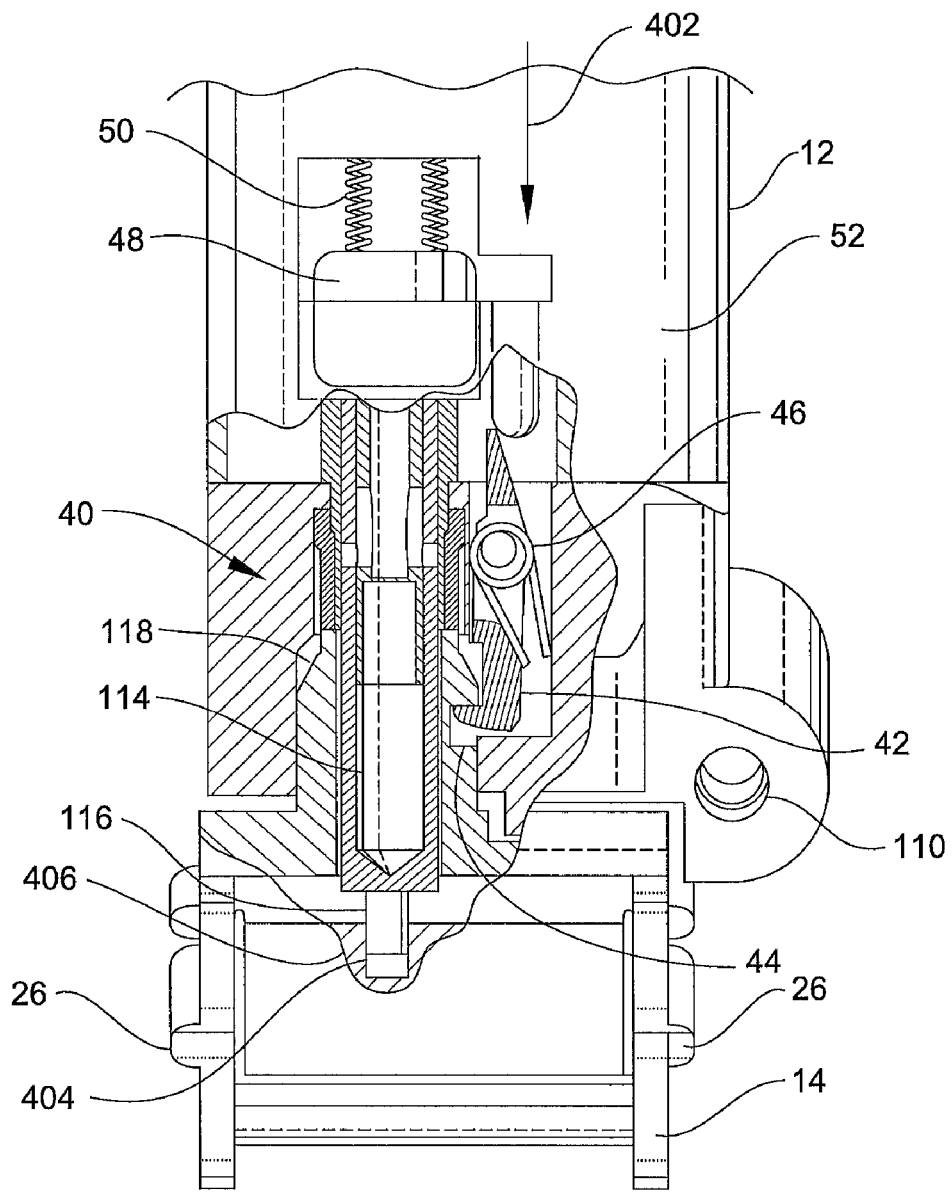
FIG. 4 is a sectional view showing a latch assembly of the microkeratome.

FIG. 4 shows a latch assembly 40 that connects the head 14 to the hand piece 12. The latch assembly 40 may include a latch 42 that is pivotally connected to the hand piece 12 and fits within the groove 44 of the head 14. In the illustrated example, the groove 44 is formed in the coupling member 118 of the head 14. The latch assembly 40 may include a return spring 46 that biases the latch 42 into the groove 44.

The latch assembly 40 may further have an actuator 48 that can be depressed by a user to move in a downward direction as indicated by an arrow 402 to rotate the latch 42 out of the groove 44. The assembly 40 may include a return spring(s) 50 to move the actuator 48 back when released by the user. As shown in FIGS. 1, 2 and 4, the actuator 48 may be located on a first face 52 of the hand piece 12.

A user can attach the head 14 to the hand piece 12 by moving the head 14 until the latch 42 snaps into the groove 44. The head 14 can be removed from the hand piece 12 by depressing the actuator 48 to pull the latch 42 out of the groove 44. The head 14 may then be sterilized and re-attached to the hand piece 12. Alternatively, the head 14 may be replaced. By way of example, the head 14 may be constructed from a low cost plastic material that is replaced after every procedure. The hand piece 12 may also be constructed from a plastic material. The head 14 may be constructed from the same plastic material as the hand piece 12. By way of example, the plastic may be a polycarbonate or polysulphone.

FIG. 4 also illustrates the shaft 114 and the eccentric pin 116 of the motor that drives the lateral oscillatory motion of the blade (or blade holder). The shaft 114 may extend through the bore of the coupling member 118 of the head 14. The eccentric pin 116 engages a slot 404 of the blade (or blade holder) 406.

Figure 5:
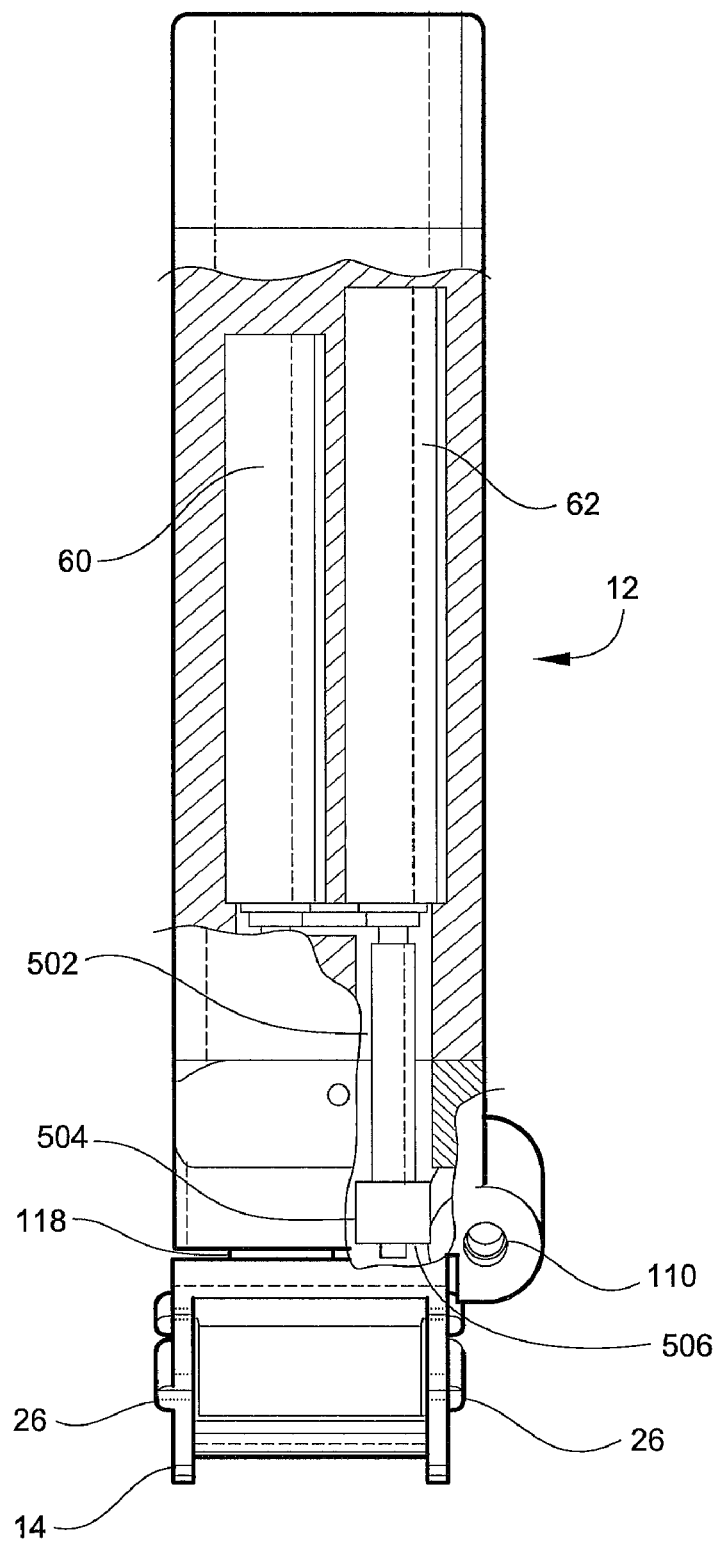
FIG. 5 is a sectional view showing motors of the microkeratome.

FIG. 5 shows a pair of motor assemblies 60 and 62 within the hand piece 12. Motor assembly 60 may move the blade in a lateral reciprocating manner. Motor assembly 62 may be coupled to the elongated helical gear 22 of the ring assembly 16 to pull the head 14 and blade across the ring opening 24. In the present context, the term "assembly" indicates one or more components (e.g., motor, shaft, linkage, gear, etc.) as needed to effect the movement of the blade in the linear and lateral directions via a source of power disposed in or coupled to the hand piece 12. In the illustrated example, the motor assembly 62 that drives the linear motion of the head 14 and blade may include a shaft 502 and one or more internal gears 504 and 506. In this example, the internal gear 506 includes threads in mating engagement with the threads of the helical gear 22. The internal gear 506 may, for example, have an annular structure in which internal threads engage the helical gear 22 and external threads engage another internal gear 504 (or directly to threads provided on the shaft 502). In this example, the helical gear 22 does not itself rotate. Consequently, the internal gear 506 functions as a rotating, linearly moving worm gear that is driven by the motor assembly 62 to travel along the length of the helical gear 22. By way of the mating engagement between the moving internal gear 506 and the stationary helical gear 22, the hand piece 12, head 14 and blade are pulled forward in the linear direction along which the helical gear 22 is oriented.

Figure 6:
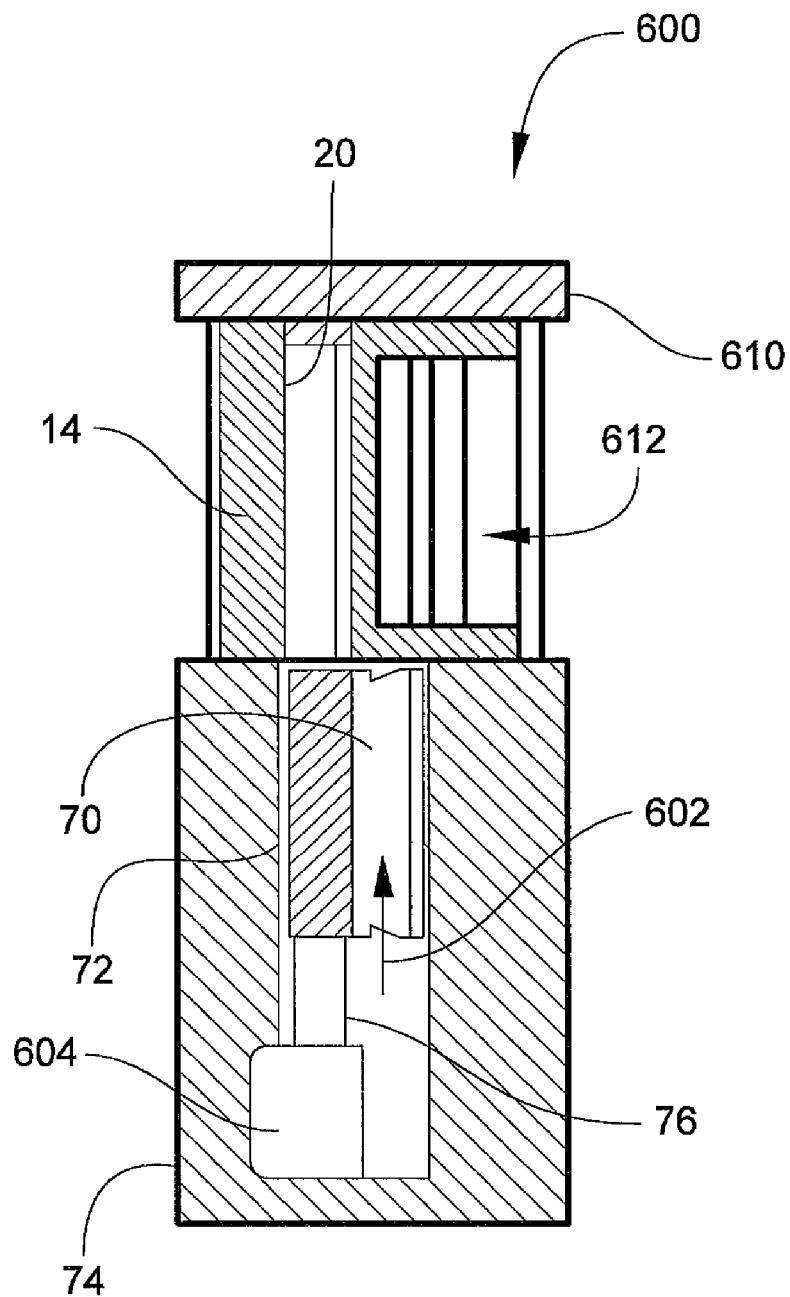
FIG. 6 is a top sectional view showing a blade being loaded into a head of the microkeratome from a blade shuttle.

As shown in FIG. 6, a blade (or a blade mounted to a blade holder) 70 may be packaged within a blade shuttle 600. The blade shuttle 600 may include a housing 74 having a housing interior 72 that holds the blade 70. In advantageous implementations, the housing 74 encloses the blade 70 in a sealed, sterile condition prior to use of the blade 70. The blade shuttle 600 may further include a plunger 76 located in the housing 74. The plunger 76 may be operated to push the blade 70 into the head 14 along a blade-loading direction 602. For this purpose, a portion 604 of the plunger 76 (e.g., a tab, button, finger grip, or the like) may be accessible from outside the housing 74 for manipulation by the user. The blade shuttle 600 may further include a drawer 610 that slides out from the housing 74 to the open position illustrated in FIG. 6. The drawer 610 has a drawer opening 612 communicating with the housing interior 72. The drawer opening 612 receives the head 14 in preparation for operating the plunger 76 to push the blade 70 into the blade cavity 20 of the head 14.

The blade shuttle 600 may have an alignment pin (not shown) that is inserted into a corresponding alignment hole (not shown) of the head 14 to align the blade 70 with the head cavity 20. The housing 74 may include a stop (not shown) that limits the travel of the plunger 76 and the location of the blade 70 within the head 14. The stop provides a feature that allows for the blade 70 to be accurately located within the head cavity 20 in a repeatable manner. It is desirable to accurately locate the blade 70 within the blade cavity 20 so that the eccentric pin 116 (FIG. 4) of the motor assembly 60 (FIG. 5) is properly coupled to the corresponding slot 404 (FIG. 4) of the blade 70.

In use, the blade shuttle 600 may be initially provided to the user as a package that contains the blade (or blade holder) 70 in a sterile condition within the housing interior 72. In this closed position, the drawer opening 612 and the blade 70 are enclosed by the housing 74. To install the blade 70 into the head 14, the user may slide out the drawer 610 from the closed position to an open position to reveal the drawer opening 612, position the head 14 in the drawer opening 612 such that the blade cavity 20 is in proper alignment with the blade 70, and operate the plunger 76 (such as by manipulating the exposed portion 604) to transfer the blade 70 from the housing 74 into the blade cavity 20. The blade shuttle 600 may be discarded thereafter.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A blade shuttle for packaging a microkeratome blade and loading the blade into a cavity of a head of a microkeratome, the blade shuttle comprising:
    a housing having a housing interior; a blade disposed in the housing interior;
    a plunger disposed in the housing interior and engaging the blade at least a portion of the plunger being accessible from outside the housing for manipulation by a user, and the plunger being slidable relative to the housing in a blade-loading direction; and
    a drawer having a drawer opening and slidable relative to the housing in the blade-loading direction from a closed position to an open position wherein, at the closed position, the drawer opening and the blade are enclosed by the housing, and at the open position, the drawer opening is adjacent to the housing interior and accessible from outside the housing, and the drawer opening is configured to receive the microkeratome head at a head position at which the head cavity is aligned with the blade along the blade-loading direction,
    wherein the plunger is mounted to the housing and slidable independently of the drawer, and sliding of the plunger in the blade-loading direction toward the drawer at the open position loads the blade from the housing interior into the drawer and into the head cavity.

2. The blade shuttle of claim 1, wherein the drawer is disposed at the open position, and further including the microkeratome head disposed in the drawer opening wherein the head cavity is aligned with the blade along the blade-loading direction.

3. The blade shuttle of claim 1, wherein the drawer is disposed at the open position, and further including the microkeratome head disposed in the drawer opening and the blade disposed in the head cavity.

4. A method for loading a microkeratome blade into a cavity of a head of a microkeratome, the method comprising:
    sliding a drawer of a blade shuttle from a closed position to an open position, the blade shuttle including a housing having an interior and enclosing the blade in the housing interior, wherein at the closed position, the blade and a drawer opening of the drawer are enclosed by the housing, and at the open position, the drawer opening is adjacent to the housing interior and accessible from outside the housing and the blade remains in the housing interior;
    inserting the microkeratome head into the drawer opening such that the head cavity is aligned with the blade along a blade-loading direction; and
    moving the blade along the blade-loading direction from the housing interior into the drawer and into the head cavity by actuating a plunger of the blade shuttle that engages the blade along the blade-loading direction toward the drawer, wherein the plunger is actuated independently of sliding the drawer.

5. The method of claim 4, further including detaching the microkeratome head from the microkeratome.

6. The method of claim 4 further including, after moving the blade into the head cavity, attaching the microkeratome head to a microkeratome.

7. The method of claim 4, wherein moving the blade comprises manipulating a portion of the plunger disposed at a location outside the housing interior.

\* \* \* \* \*